(12) United States Patent
MacPhee et al.

(10) Patent No.: US 7,217,535 B2
(45) Date of Patent: *May 15, 2007

(54) LIPOPROTEIN ASSOCIATED PHOSPHOLIPASE A2, INHIBITORS THEREOF AND USE OF THE SAME IN DIAGNOSIS AND THERAPY

(75) Inventors: Colin H. MacPhee, Berwyn, PA (US); David Graham Tew, Leicester (GB)

(73) Assignee: SmithKline Beecham P.L.C., Brentford, Middlesex (GB)

( * ) Notice: Subject to any disclaimer, the term of this patent is extended or adjusted under 35 U.S.C. 154(b) by 149 days.

This patent is subject to a terminal disclaimer.

(21) Appl. No.: 10/973,467

(22) Filed: Oct. 26, 2004

(65) Prior Publication Data

US 2005/0106611 A1 May 19, 2005

Related U.S. Application Data

(63) Continuation of application No. 10/173,233, filed on Jun. 14, 2002, now Pat. No. 7,052,862, which is a continuation of application No. 09/569,899, filed on May 12, 2000, which is a continuation of application No. 09/294,384, filed on Apr. 20, 1999, now Pat. No. 6,177,257, which is a continuation of application No. 08/387,858, filed as application No. PCT/GB94/01374 on Jun. 24, 1994, now Pat. No. 5,981,252.

(30) Foreign Application Priority Data

Jun. 25, 1993 (GB) .................................. 9313144.9
Jan. 11, 1994 (GB) .................................. 9400413.2

(51) Int. Cl.
*C12Q 1/34* (2006.01)

(52) U.S. Cl. ........................... 435/18; 435/4; 435/198; 435/252.3; 435/320.1

(58) Field of Classification Search ................ 435/18, 435/198, 252.3, 320.1, 4
See application file for complete search history.

(56) References Cited

U.S. PATENT DOCUMENTS

| | | | |
|---|---|---|---|
| 5,019,508 A | 5/1991 | Johnson et al. ............. 435/198 |
| 5,108,899 A | 4/1992 | Allen ........................ 435/7.21 |
| 5,210,017 A | 5/1993 | Carlsson et al. ............. 435/7.8 |
| 5,279,957 A | 1/1994 | Gross ...................... 435/240.2 |
| 5,527,698 A | 6/1996 | Knopf et al. |
| 5,530,101 A | 6/1996 | Queen et al. ............. 530/387.3 |
| 5,532,152 A | 7/1996 | Cousens et al. |
| 5,605,801 A | 2/1997 | Cousens et al. |
| 5,641,669 A | 6/1997 | Cousens et al. |
| 5,656,431 A | 8/1997 | Cousens et al. |
| 5,698,403 A | 12/1997 | Cousens et al. |
| 5,847,088 A | 12/1998 | Cousens et al. |
| 5,880,273 A | 3/1999 | Adachi et al. |
| 5,968,818 A | 10/1999 | Gloger et al. |
| 5,977,308 A | 11/1999 | Cousens et al. |
| 5,981,252 A | 11/1999 | MacPhee et al. |
| 6,045,794 A | 4/2000 | Cousens et al. |
| 6,099,836 A | 8/2000 | Cousens et al. |
| 6,146,625 A | 11/2000 | Cousens et al. |
| 6,177,257 B1* | 1/2001 | Macphee et al. ............. 435/7.4 |
| 6,203,790 B1 | 3/2001 | Cousens et al. |
| 7,045,329 B2 | 5/2006 | MacPhee et al. ............. 435/198 |
| 7,052,862 B2* | 5/2006 | MacPhee et al. ............. 435/18 |

FOREIGN PATENT DOCUMENTS

| | | |
|---|---|---|
| EP | 359425 | 8/1989 |
| EP | 509719 | 10/1992 |
| EP | 658205 | 3/2000 |
| EP | 673426 | 6/2001 |
| JP | 04346797 | 8/1988 |
| JP | 07059597 | 10/1989 |
| JP | 04346797 | 12/1992 |
| JP | 07059597 | 3/1995 |
| JP | 10017600 | 1/1998 |
| WO | WO 89/09818 | 10/1989 |
| WO | WO 94/20069 | 9/1994 |
| WO | WO 95/00649 | 1/1995 |
| WO | WO 95/09921 | 4/1995 |
| WO | WO 97/12984 | 4/1997 |
| WO | WO 98/44158 | 10/1998 |
| WO | WO 99/09147 | 2/1999 |
| WO | WO 99/64627 | 12/1999 |

(Continued)

OTHER PUBLICATIONS

Yamamoto et al. (1990) Formation of lipid hydroperoxides in the cupric ion-induced oxidation of plasma and low density lipoprotein. Oxid. Damage Repair, Int. Soc. Free Radical Res. Bienn. Meeting. Meeting Date 1990, pp. 287-291. Editor: K. J. A. Da, Jan. 1990.
Stafforini et al., "The Platelet-activating Factor Acetylhydrolase from human erythrocytes", Journal of Biological Chemistry 1993 vol. 268; 6; 3856-3865.
Stafforini et al., "Platelet activating factor acetylhydrolase from human plasma", Methods in Enzymology 1990 187: 344-57. Kohler G, et al., Nature 256:495-497 (1975).
Sevier, Ed, et al., Clinical Chem. 27:1797-1806 (1981).
Chandrakumar NS, et al.; :Stereospecific Synthesis of Ehter Phospholipids. Preparation of a-Alkyl-2-(acylamino)-2 deoxyglycerophosphoryl cholines, J. Org. Chem., 1197-1202 (1983).
Ponpipom MM, et al., Synthesis of Azide and Amide Analogs of Platelet-Activating Factors and Related Derivatives, Chem. Phys. Lipids;35:29-37 (1984).

(Continued)

*Primary Examiner*—Tekchand Saidha
(74) *Attorney, Agent, or Firm*—Licata & Tyrrell P.C.; Nathan P. Letts

(57) ABSTRACT

The enzyme $Lp\text{-}PLA_2$ in purified form, an isolated nucleic acid molecule encoding $Lp\text{-}PLA_2$, the use of an inhibitor of the enzyme $Lp\text{-}PLA_2$ in therapy and a method of screening compounds to identify those compounds.

27 Claims, 2 Drawing Sheets

FOREIGN PATENT DOCUMENTS

Figure 1:
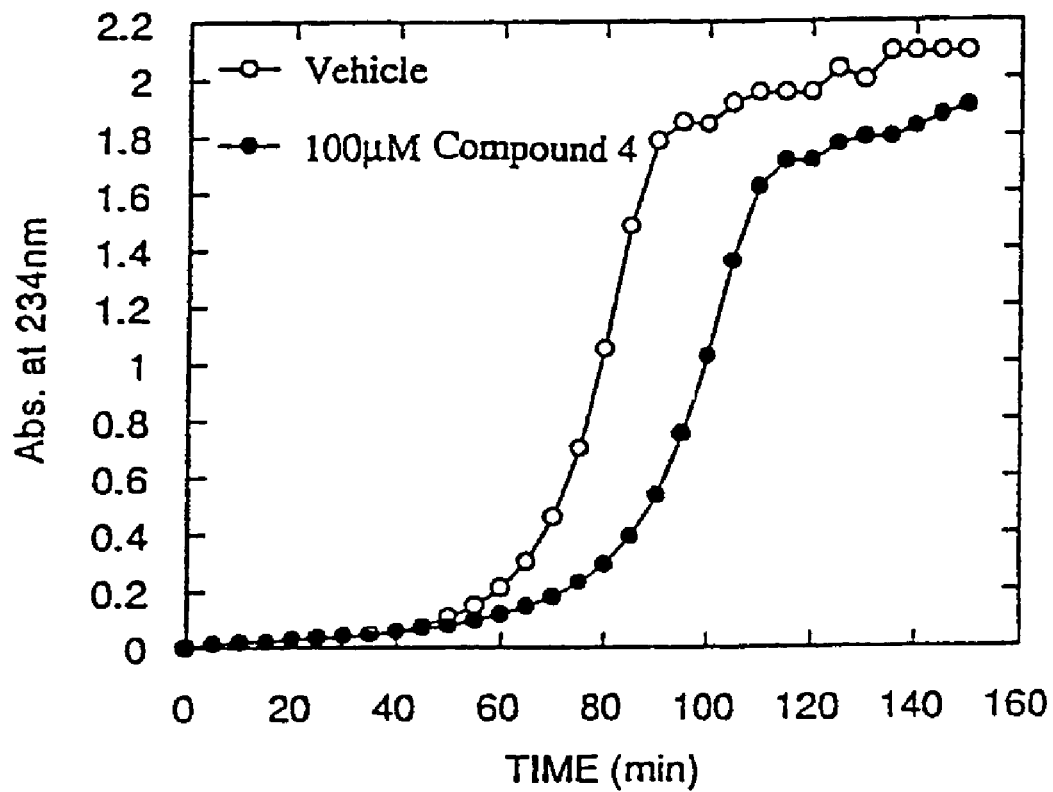

| | | |
|---|---|---|
| WO | WO 00/24910 | 5/2000 |
| WO | WO 00/32808 | 6/2000 |

OTHER PUBLICATIONS

Stafforini D, et al., "Human plasma platelet-activating factor acetylhydrolase," J. Biol. Chem. 262(9): 4224-4230 (1987).

Stafforini D, et al. "Human macrophages secrete plate-activating factor actylhydrolase," J. Biol. Chem. 265(17):9682-9687 (1990).

Langlais J. et al., Platelet-activating factor acetyl-hydrolase in human semen:a novel decapacitation factor? Biol. of Reprod. 44 (Suppl. 1):94 (1991).

San H, et al. "Safety and Short Term Toxicity of a Novel and Cationic Formulation for Human Gene Therapy," Human Gene Therapy: 781-798 (1993).

Kim UT, et al. "Synthesis of Phospholipid Head groups via Nucleophilic Ring Opening of 1.3.2-Dioxaphospholanes," J. Chem. Commun.: 70-71 (1993).

Christoffersen R, et al. "Ribozymes as Human Theraputic Agents," J. of Medicinal Chem.: 2023-2037 (1994).

Stull R, et al., "Antigene, Ribozyme, and Aptomer Nucleic Acid Drugs: Progress and Prospects," Pharm. Res. 1995.

Kohler G, et al., 256:495-497 (1975).

U.S. Appl. No. 08/886,152, filed Jun. 18, 1996, related to ref. AW of Oct. 26, 2004 IDS.

Hirashima et al., "Platelet-activating factor (PAF) concentration and PAF acetylhydrolase activity in cerebrospinal fluid of patients with subarachnoid hemorrhage", J. Neurosurg 1994 80:31-36.

Kuby, Janis, "Immunology" 1991 W.H. Freeman 80-83.

Satoh et al., "Platelet-Activating Factor Acetylhydrolase in Plasma Lipoproteins From Patients With Ischemic Stroke", Stroke 1992 23:1090-1092.

Satoh et al., "Activity of Platelet-Activating Factor (PAF) Acetylhydrolase in Plasma from Patients with Ischemic Cerebrovascular Disease", Prostaglandins 1988 35 (5) :685-698.

Stafforini et al., "Platelet-activating Factor Acetylhydrolases", J. Biol. Chem. 1997 272(29) :17895-17898.

Washburn, W.N. and Dennis, E.A. "Novel General Approach for the Assay and Inhibition of Hydrolytic Enzymes Utilizing Suicide-Inhibitory Bifunctional Linked substrates (SIBLINKS) :Exemplified in a Phospholipase Assay" J. Am. Chem. Soc. 1990 112:2040-2041.

Washburn, W.N. and Dennis, E.A. "Suicide-inhibitory Bifunctionally Linked Substrates (SIBLINKS) as Phospholipase A2 Inhibitors" J. Biol. Chem. 1991 266(8) :5042-5048.

Yoshida et al., "Platelet-activating factor acetylhydrolase activity in red blood cell-stroma from patients with cerebral thrombosis", Acta Neurol Scand 1992 86:199-203.

Adjei et al., "Pulmonary Delivery of Peptide Drugs: Effect of Particle Size on Bioavailability of Leuprolide Acetate in Healthy Male Volunteers", Pharm. Res. 7(6):565-569 (1990).

Basran et al., "Properties of Platelet Activating Factor (PAF-ACETHER) Which Suggest Involvement in Chronic Inflammation and Persistent Asthma", Br. J. Pharmacol. 77:437 (1982).

Braquet et al., "Effect of Endothelin-1 on Blood Pressure and Bronchopulmonary System of the Guinea Pig", J. Cardio. Pharm. 13 (Supp.5):S143-S146 (1989).

Brenner, "The Molecular Evolution of Genes and Proteins: A Tale of Two Serines", Nature 334:528-530 (1988).

Campbell, Biology 3rd Ed., p. 104-106 (1993).

Capecchi, "Altering the Genome by Homologous Recombination", Science 244:1288-1292 (1989).

Caplan et al., "Role of Platelet Activating Factor and Tumor Necrosis Factor-alpha in Neonatal NecrotizingEnterocolitis", J. Pediatr. 116(6):960-964 (1990).

Chapus et al., "Minireview on Pancreatic Lipase and Colipase", Biochimie 70:1223-1234 (1988).

deBoer et al., "The tac Promoter: A Functional Hybrid Derived from the trp and lac Promoters", Proc. Natl. Acad. Sci. USA 80:21-25 (1983).

Debs et al., "Lung-Specific Delivery of Cytokines Induces Sustained Pulmonary and Systemic Immunomodulation in Rats", J. Immunol. 140(10):3482-3488 (1988).

Denizot et al., "PAF-Acether and Acetylhydrolase in Stool of Patients with Crohn's Disease", Digestive Diseases and Sciences 37(3):432-437 (1992).

Furukawa et al., "Platelet-activating Factor-induced Ischemic Bowel Necrosis: The Effect of Platelet-Activating Factor Acetylhydrolase", Ped. Res. 34(2):237-241 (1993).

Grino J.M., "BN 52021:A Platelet Activating Factor Antagonist for Preventing Post-Transplant Renal Failure", Ann. Int. Med. 121(5):345-347 (1994).

Hahn et al., "The Complete Sequences of Plasmids pFNeo and pMH-Neo: Convenient Expression Vectors for High-level Expression of Eukaryotic Genes in Hematopoietic Cell Lines", Gene 127:267-268 (1993).

Harlow et al., "Antibodies: A Laboratory Manual", Cold Spring Harbor Press, p. 423 (1988).

Handley et al., "Platelet Activating Factor and Inflammation in Atherogenesis: Targets for Drug Development", Drug Dev. Res. 7:361-375 (1986).

Hattori et al., "The Catalytic Subunit of Bovine Brain Platelet-activating Factor Acetylhydrolase is a Novel Type of Serine Esterase", J. Biol. Chem. 269(37):23150-23155 (1994).

Hattori et al., "Purification and Characterization of Bovine Brain Platelet-activating Factor Acetylhydrolase", J. Biol. Chem. 268(25):18748-18753 (1993).

Henriques et al., "Endothelin-1 Inhibits PAF-induced Paw Oedema and Pleurisy in the Mouse",Br. J. Pharmacol. 106-579-582 (1992).

Heuer et al., "Current Status of PAF Antagonist", Clin. Exp. Allergy 22:980-983 (1992).

Hoffman et al., "Detection of Platelet-activating Factor in Amniotic Fluid of Complicated Pregnancies", Am. J. Obstet Gynecol. 162(2):525-528 (1990).

Horwitz et al., "DNA Sequence of the araBAD-araC Controlling Region in *Salmonella typhimurium* LT2", Gene 14:309-319 (1981).

Hsieh et al., "Increased Plasma Platelet-activating Factor in Children with Acute Asthmatic Attacks and Decreased in vivo and in vitro Production of Platelet-activating Factor After Immunotherapy", J. Allergy Clin. Immunol. 91:650-657 (1993).

Hsueh et al., "Platelet-activating Factor, Tumor Necrosis Factor, Hypoxia and Necrotizing Enterocolitis", Acta Paediatr. Suppl. 396:11-17 (1994).

Hubbard et al., "Anti-Neutrophil-Elastase Defenses of the Lower Respiratory Tract in alpha1-Antitrypsin Deficiency Directly Augmented with an Aerosol of A-1-Antitrypsin", Ann. Int. Med. 111(3):206-212 (1989).

Kald et al., "Release of Platelet-Activating Factor in Acute Experimental Pancreatis", Pancreas 8(4):440-442 (1993).

Kirsch et al., "Mechanism of Platelet Activating Factor-Induced Vascular Leakage in the Rat Trachea", Exp. Lung Res. 18:447-459 (1992).

Kurosawa et al., "Increased Levels of Blood Platelet-activating Factor in Bronchial Asthmatic Patients with Active Symptoms", Allergy 49:60-63 (1994).

LaVallie et al., "A Thioredoxin Gene Fusion Expression System That Circumvents Inclusion Body Formation in the *E. coli* Cytoplasm", Bio/Technology 11:187-193 (1993).

Lellouch-Tubiana et al., "Eosinophil Recruitment into Guinea Pig Lungs after PAF-acether and Allergen Administration", Am. Rev. Respir. Dis. 137:948-954 (1988).

Lellouch-Tubiana et al., "Ultrastructural Evidence for Extravascular Platelet Recruitment in the Lung upon Intravenous Injection of Platelet-activating Factor (PAF-acether) to Guinea-pigs", Br. J. Exp. Path. 66:345-355 (1985).

Lewin B., Genes V, Oxford University Press, New York, New York, Chapter 6, pp. 136-141 (1994).

Lindsberg et al., "Evidence for Platelet-Activating Factor as a Novel Mediator in Experimental Stroke in Rabbits", Stroke 21:1452-1457 (1990).

Lindsberg et al., "Platelet-activating Factor in Stroke And Brain Injury", Ann. Neurol. 30(2):117-129 (1991).

Maki et al., "Platelet-activating Factor Acetylhydrolase Activity in Maternal, Fetal, and Newborn Rabbit Plasma During Pregnancy and Lactation", Proc. Natl. Acad. Sci. USA 85:728-732 (1988).

Matsumoto et al., "Platelet-Activating Factor in Bronchoalveolar Lavage Fluid of Patients with Adult Respiratory Distress Syndrome", Clin. Exp. Pharmacol. Physiol. 19:509-515 (1992).

Matsuzaki et al., "PAF Acetylhydrolase Activities in Human Systemic Lupus Erythematosus and Lupus-Prone Mice", Clinica Chimica Acta 210:139-144 (1992).

Mezzano et al., "Detection of Platelet-Activating Factor in Plasma of Patients with *Streptococcal nephritis*", J. Am. Soc. Nephrol. 4:235-242 (1993).

Miwa et al., "Characterization of Serum Platelet-activating Factor (PAF) Acetylhydrolase", J. Clin. Invest. 82:1983-1991 (1988).

Rabinovici et al., "Platelet Activating Factor Mediates Interleukin-2-induced Lung Injury in the Rat", J. Clin. Invest. 89:1669-1673 (1992).

Rabinovici et al., "ARDS-like Lung Injury Produced by Endotoxin in Platelet-activating Factor-primed Rats", J. Appl. Physiol. 74(4):1791-1802 (1993).

Rodriguez-Roisin et al., "Platelet-activating Factor Causes Ventilation-Perfusion Mismatch in Humans", J. Clin. Invest. 93:188-194 (1994).

Roitt et al., Immunology, Gower Medical Publishing Co., p. 25.7 (1985).

Sandhu et al., "Amplification of Reproducible Allele Markets for Amplified Fragment Length Polymorphism Analysis", Biotechniques 12(1):16-22 (1992).

Satoh et al., "Platelet-activating Factor (PAF) Stimulates the Production of PAF Acetylhydrolase by the Human Hepatoma Cell Line, HepG2", J. Clin. Invest. 87:476-481 (1991).

Smith et al., "Pulmonary Deposition and Clearance of Aerosolized Alpha-1-Proteinase Inhibitor Administered to Dogs and to Sheep", J. Clin. Invest. 84:1145-1154 (1989).

Stafforini et al., "Human Plasma Platelet-activating Factor Acetylhydrolase: Association with Lipoprotein Particles andRole in the Degradation of Platelet-activating Factor", J. Biol. Chem. 262(9):4215-4222 (1987).

Stafforini et al., "Platelet-activating Factor Acetylhydrolase Activity in Human Tissues and Blood Cells", Lipids, 26(12):979-985 (1991).

Stafforini et al., "Lipoproteins Alter the Catalytic Behavior of the Platelet-activating Factor Acetylhydrolase in Human Plasma", Proc. Natl. Acad. Sci. USA 86:2393-2397 (1989).

Stremler et al., "An Oxidized Derivative of Phosphatidylcholine Is a Substrate for the Platelet-activating Factor Acetylhydrolase from Human Plasma," J. Biol. Chem. 264(10): 5331-5334 (1989).

Stremler et al., "Human Plasma Platelet-activating Factor Acetylhydrolase", J. Biol. Chem. 266(17):11095-11103 (1991).

Tarbet et al., "Liver cells Secrete the Plasma Form of Platelet-activating Factor Acetylhydrolase", J. Biol. Chem. 266(25):16667-16673 (1991).

Tjoelker et al., "Anti-inflammatory Properties of a Platelet-activating Factor Acetylhydrolase", Nature 374:549-553 (1995).

Venable et al., "Platelet-activating Factor: a Phospholipid Autacoid with Diverse Actions", J. Lipid Res. 34:691-702 (1993).

Von Heijne, "A New Method for Predicting Signal Sequence Cleavage Sites", Nuc. Acids. Res. 14(11):4683-4690 (1986).

Wada et al., "Codon Usage Tabulated from the GenBank Genetic Sequence Data", Nuc. Acids Res. 19S:1981-1986 (1991).

Watanabe et al., "Pharmacological Analysis of Neutrophil Chemotactic Factor Production by Leucocytes and Roles of PAF in Allergic Inflammation in Rats", Br. J. Pharmacol. 111:123-130 (1994).

Watson et al., "The Platelet-Activating Factor Antagonist Web 2170; Its Beneficial Effect on Dog Renal Allograft Survival", Transplantation 56(4):1047-1049 (1993).

Yasuda et al., "The Hormonal Regulation of Platelet-Activating Factor-Acetylhydrolase in the Rat", Endocrinology 130(2):708-716 (1992).

Zarco et al., "Involvement of Platelet-activating Factor and Tumour Necrosis Factor in the Pathogenesis of Joint Inflammation in Rabbits", Clin. Exp. Immunol. 88:318-323 (1992).

Elstad et al., "Platelet-activating Factor Acetylhydrolase Increases during Macrophage Differentiation" J. Biol. Chem. 264:8467-8470 (1989).

Smiley et al., "Oxidatively Fragmented Phosphatidylcholines Activate Human Neutrophils through the Receptor for Platelet-activating Factor," J. Biol. Chem. 266:11104-11110 (1991).

Tjoelker et al., "Plasma Platelet-activating Factor Acetylhydrolase is a Secreted Phospholipase A2 with a Catalytic Triad," J. Biol. Chem. 270:25481-25487 (1995).

Yasuda et al., "Influence of a Cigarette Smoke Extract on the Hormonal Regulation of Platelet-activating Factor Acetylhydrolase in Rats," Biol. Repro. 53:244-252 (1995).

Sigma-Aldrich Catalog Product Detail, PAF (2005).

* cited by examiner

Fig.1 Compound 4 inhibits copper (5μM) - stimulated LDL (150μg/ml) oxidation.

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
        (A) LENGTH: 37 amino acids
        (B) TYPE: amino acid
        (C) STRANDEDNESS: <Unknown>
        (D) TOPOLOGY: linear (ii) MOLECULE TYPE: peptide (iii) HYPOTHETICAL: NO (v) FRAGMENT TYPE: internal (vi) ORIGINAL SOURCE:

(ix) FEATURE:

(xi) SEQUENCE DESCRIPTION: SEQ ID NO: 1:

```
Met Leu Lys Leu Lys Gly Asp Ile Asp Ser Asn Ala Ala Ile Asp Le
1               5                  10                  15

Ser Asn Lys Ala Ser Leu Ala Phe Leu Gln Lys His Leu Gly Leu Hi
                20                  25                  30

Lys Asp Phe Asp Gln
            35
```

(2) INFORMATION FOR SEQ ID NO: 2:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 2:

```
Trp Met Phe Pro Leu Gly Asp Glu Val Tyr Ser Arg Ile Pro Gln Pr
1               5                  10                  15

Leu Phe Phe Ile Asn Ser Glu Tyr Phe Gln Tyr Pro Ala Asn
                20                  25                  30
```

(2) INFORMATION FOR SEQ ID NO: 3:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 3:

Gln Tyr Ile Asn Pro Ala Val Met Ile Thr Ile Arg Gly Ser Val Hi
1               5                   10                  15

Gln Asn Phe Ala Asp Phe Thr Phe Ala Thr Gly
            20                  25

(2) INFORMATION FOR SEQ ID NO: 4:

(i) SEQUENCE CHARACTERISTICS:
            (A) LENGTH: 19 amino acids
            (B) TYPE: amino acid
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 4:

Trp Leu Met Gly Asn Ile Leu Arg Leu Leu Phe Gly Ser Met Thr Th
1               5                   10                  15

Pro Ala Asn (2) INFORMATION FOR SEQ ID NO: 5:

(i) SEQUENCE CHARACTERISTICS:
            (A) LENGTH: 420 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 5:

AAAAAACCTA TTTTAATCCT AATTGTATTT CTCTATTCCT GAAGAGTTCT GTAACATGAT      60

GTGTTGATTG GTTGTGTTAA TGTTGGTCCC TGGAATAAGA TTCTCATCAT CTCCTTCAA     120

CAAGCAGTCC CACTGATCAA ATCTTTATG AAGTCCTAAA TGCTTTTGTA AGAATGCTA      180

TGAAGCTTTG TTGCTAAGAT CAATAGCTGC ATTTGAATCT ATGTCTCCCT TTAATTTGA     240

CATGTGTCCA ATTATTTTGC CAGTNGCAAA AGTGAAGTCA GCAAAATTCT GGTGGACTG     300

ACCCCTGATT GTAATCATCT TTCTTTCTTT ATCAGGTGAG TAGCATTTTT TCATTTTTA     360

GATATTAGCA GGATATTGGA AATATTCAGN GTTGNTAAAA AGNGGNGGCT GAGGGATTC     420

(2) INFORMATION FOR SEQ ID NO: 6:

(i) SEQUENCE CHARACTERISTICS:
            (A) LENGTH: 379 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 6:

| | | | | | |
|---|---|---|---|---|---|
| TGCTAATATC | ATAAAAATGA | AAAAATGCTA | CTCACCTGAT | AAAGAAAGAA | AGATGATTAC | 60
| AATCAGGGGT | TCAGTCCACC | AGANTTTTGC | TGACTTCACT | TTTGCAACTG | GCAAAATAA | 120
| TGGACACATG | CTCAAATTAA | AGGGAGACAT | AGATTCAAAT | GTAGCTATTG | ATCTTAGCA | 180
| CAAAGCTTCA | TTAGCATTCT | TACAAAAGCA | TTTAGGACTT | CATAAAGATT | TTGTTCAGT | 240
| GGACTGCTTG | ATTGAAGGAG | ATGATGAGAA | TCTTATTCCA | GGGACCAACA | TTAACACAA | 300
| CAATTCAACA | CATCATGTTT | ACAGAACTTC | TTCCAGGGAA | TAGGAGGAAA | TACAATTGG | 360
| GTTTAAAATA | GGTTTTTTT | | | | | 379

(2) INFORMATION FOR SEQ ID NO: 7:

(i) SEQUENCE CHARACTERISTICS:
        (A) LENGTH: 279 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 7:

| | | | | | |
|---|---|---|---|---|---|
| GAAGAATGCA | TTAGATTTAA | AGTTTGATAT | GGAACAACTG | AAGGACTCTA | TTGATAGGGA | 60
| AAAAATAGCA | GTAATTGGAC | ATTCTTTTGG | TGGAGCAACG | GTTATTCAGA | CTCTTAGTG | 120
| AGATCAGAGA | TTCAGATGTG | GTATTGCCCT | GGATGCATGG | ATGTTTCCAC | TGGGTGATG | 180
| AGTATATTCC | AGAATTCCTC | AGCCCCTCTT | TTTTATCAAC | TCTGAATATT | TCCAATATC | 240
| TGCTAATATC | ATAAAANTGG | AAAAATGCTA | CTCACCTGG | | | 279

(2) INFORMATION FOR SEQ ID NO: 8:

(i) SEQUENCE CHARACTERISTICS:
        (A) LENGTH: 572 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 8:

| | | | | | |
|---|---|---|---|---|---|
| AAAATAGCAG | TAATTGGACA | TTCTTTAGGT | GGAGCAACGG | TTATTCAGAC | TCTTAGTGAA | 60
| GATCAGAGAT | TCAGATGTGG | TATTGCCCTG | GATGCATGGA | TGTTTCCACT | GGGTGATGA | 120
| GTATATTCCA | GAATTCCTCA | GCCCCTCTTT | TTTATCAACT | CTGAATATTT | CCAATATCC | 180
| GCTAATATCA | TAAAAATGAA | AAATGCTAC | TCACCTGATA | AGAAAGAAA | GATGATTAC | 240
| ATCAGGGGTT | CAGTCCACCA | GAATTTTGCT | GACTTCACTT | TTGCAACTGG | CAAAATAAT | 300
| GGACACATGC | TCAAATTAAA | GGGAGACATA | GATTCAAATG | TAGCTATTGA | TCTTAGCAA | 360
| AAAGCTTCAT | CAGCATTCTT | ACAAAAGCAT | TTAGGACTTC | ATAAAGATTT | TGATCAGTG | 420
| GACTGCTTGA | TTGAAGGAGA | TGATGAGAAT | CTTATTCCAG | GGACCAACAT | TAACACAAC | 480
| AATCAACACA | TCATGTTACA | GAACTCTTCA | GGAATAGAGA | AATACAATTA | GGATTAAAA | 540
| AGGTTTTTTA | AAAAAAAAAA | AAAAAAAACT | CG | | | 572

(2) INFORMATION FOR SEQ ID NO: 9:

(i) SEQUENCE CHARACTERISTICS:
　　　　(A) LENGTH: 1361 base pairs
　　　　(B) TYPE: nucleic acid
　　　　(C) STRANDEDNESS: double
　　　　(D) TOPOLOGY: linear (ii) MOLECULE TYPE: cDNA (iii) HYPOTHETICAL: NO (iv) ANTI-SENSE: NO (ix) FEATURE:
　　　　(A) NAME/KEY: CDS
　　　　(B) LOCATION: 38..1360

(xi) SEQUENCE DESCRIPTION: SEQ ID NO: 9:

```
TGAGAGACTA AGCTGAAACT GCTGCTCAGC TCCCAAG ATG GTG CCA CCC AAA TTG       55
                                         Met Val Pro Pro Lys Leu
                                           1               5

CAT GTG CTT TTC TGC CTC TGC GGC TGC CTG GCT GTG GTT TAT CCT TTT       103
His Val Leu Phe Cys Leu Cys Gly Cys Leu Ala Val Val Tyr Pro Phe
             10                  15                  20

GAC TGG CAA TAC ATA AAT CCT GTT GCC CAT ATG AAA TCA TCA GCA TGG       151
Asp Trp Gln Tyr Ile Asn Pro Val Ala His Met Lys Ser Ser Ala Trp
             25                  30                  35

GTC AAC AAA ATA CAA GTA CTG ATG GCT GCT GCA AGC TTT GGC CAA ACT       199
Val Asn Lys Ile Gln Val Leu Met Ala Ala Ala Ser Phe Gly Gln Thr
     40                  45                  50

AAA ATC CCC CGG GGA AAT GGG CCT TAT TCC GTT GGT TGT ACA GAC TTA       247
Lys Ile Pro Arg Gly Asn Gly Pro Tyr Ser Val Gly Cys Thr Asp Leu
 55                  60                  65                  70

ATG TTT GAT CAC ACT AAT AAG GGC ACC TTC TTG CGT TTA TAT TAT CCA       295
Met Phe Asp His Thr Asn Lys Gly Thr Phe Leu Arg Leu Tyr Tyr Pro
             75                  80                  85

TCC CAA GAT AAT GAT CGC CTT GAC ACC CTT TGG ATC CCA AAT AAA GAA       343
Ser Gln Asp Asn Asp Arg Leu Asp Thr Leu Trp Ile Pro Asn Lys Glu
             90                  95                 100

TAT TTT TGG GGT CTT AGC AAA TTT CTT GGA ACA CAC TGG CTT ATG GGC       391
Tyr Phe Trp Gly Leu Ser Lys Phe Leu Gly Thr His Trp Leu Met Gly
            105                 110                 115

AAC ATT TTG AGG TTA CTC TTT GGT TCA ATG ACA ACT CCT GCA AAC TGG       439
Asn Ile Leu Arg Leu Leu Phe Gly Ser Met Thr Thr Pro Ala Asn Trp
 120                 125                 130

AAT TCC CCT CTG AGG CCT GGT GAA AAA TAT CCA CTT GTT GTT TTT TCT       487
Asn Ser Pro Leu Arg Pro Gly Glu Lys Tyr Pro Leu Val Val Phe Ser
135                 140                 145                 150

CAT GGT CTT GGG GCA TTC AGG ACA CTT TAT TCT GCT ATT GGC ATT GAC       535
His Gly Leu Gly Ala Phe Arg Thr Leu Tyr Ser Ala Ile Gly Ile Asp
             155                 160                 165

CTG GCA TCT CAT GGG TTT ATA GTT GCT GCT GTA GAA CAC AGA GAT AGA       583
Leu Ala Ser His Gly Phe Ile Val Ala Ala Val Glu His Arg Asp Arg
             170                 175                 180

TCT GCA TCT GCA ACT TAC TAT TTC AAG GAC CAA TCT GCT GCA GAA ATA       631
Ser Ala Ser Ala Thr Tyr Tyr Phe Lys Asp Gln Ser Ala Ala Glu Ile
             185                 190                 195

GGG GAC AAG TCT TGG CTC TAC CTT AGA ACC CTG AAA CAA GAG GAG GAG       679
Gly Asp Lys Ser Trp Leu Tyr Leu Arg Thr Leu Lys Gln Glu Glu Glu
 200                 205                 210

ACA CAT ATA CGA AAT GAG CAG GTA CGG CAA AGA GCA AAA GAA TGT TCC       727
```

```
Thr His Ile Arg Asn Glu Gln Val Arg Gln Arg Ala Lys Glu Cys Ser
215                 220                 225                 230

CAA GCT CTC AGT CTG ATT CTT GAC ATT GAT CAT GGA AAG CCA GTG AAG      775
Gln Ala Leu Ser Leu Ile Leu Asp Ile Asp His Gly Lys Pro Val Lys
                235                 240                 245

AAT GCA TTA GAT TTA AAG TTT GAT ATG GAA CAA CTG AAG GAC TCT ATT      823
Asn Ala Leu Asp Leu Lys Phe Asp Met Glu Gln Leu Lys Asp Ser Ile
                250                 255                 260

GAT AGG GAA AAA ATA GCA GTA ATT GGA CAT TCT TTT GGT GGA GCA ACG      871
Asp Arg Glu Lys Ile Ala Val Ile Gly His Ser Phe Gly Gly Ala Thr
            265                 270                 275

GTT ATT CAG ACT CTT AGT GAA GAT CAG AGA TTC AGA TGT GGT ATT GCC      919
Val Ile Gln Thr Leu Ser Glu Asp Gln Arg Phe Arg Cys Gly Ile Ala
        280                 285                 290

CTG GAT GCA TGG ATG TTT CCA CTG GGT GAT GAA GTA TAT TCC AGA ATT      967
Leu Asp Ala Trp Met Phe Pro Leu Gly Asp Glu Val Tyr Ser Arg Ile
295                 300                 305                 310

CCT CAG CCC CTC TTT TTT ATC AAC TCT GAA TAT TTC CAA TAT CCT GCT     1015
Pro Gln Pro Leu Phe Phe Ile Asn Ser Glu Tyr Phe Gln Tyr Pro Ala
                315                 320                 325

AAT ATC ATA AAA ATG AAA AAA TGC TAC TCA CCT GAT AAA GAA AGA AAG     1063
Asn Ile Ile Lys Met Lys Lys Cys Tyr Ser Pro Asp Lys Glu Arg Lys
                330                 335                 340

ATG ATT ACA ATC AGG GGT TCA GTC CAC CAG AAT TTT GCT GAC TTC ACT     1111
Met Ile Thr Ile Arg Gly Ser Val His Gln Asn Phe Ala Asp Phe Thr
            345                 350                 355

TTT GCA ACT GGC AAA ATA ATT GGA CAC ATG CTC AAA TTA AAG GGA GAC     1159
Phe Ala Thr Gly Lys Ile Ile Gly His Met Leu Lys Leu Lys Gly Asp
        360                 365                 370

ATA GAT TCA AAT GCA GCT ATT GAT CTT AGC AAC AAA GCT TCA TTA GCA     1207
Ile Asp Ser Asn Ala Ala Ile Asp Leu Ser Asn Lys Ala Ser Leu Ala
375                 380                 385                 390

TTC TTA CAA AAG CAT TTA GGA CTT CAT AAA GAT TTT GAT CAG TGG GAC     1255
Phe Leu Gln Lys His Leu Gly Leu His Lys Asp Phe Asp Gln Trp Asp
                395                 400                 405

TGC TTG ATT GAA GGA GAT GAT GAG AAT CTT ATT CCA GGG ACC AAC ATT     1303
Cys Leu Ile Glu Gly Asp Asp Glu Asn Leu Ile Pro Gly Thr Asn Ile
                410                 415                 420

AAC ACA ACC AAT CAA CAC ATC ATG TTA CAG AAC TCT TCA GGA ATA GAG     1351
Asn Thr Thr Asn Gln His Ile Met Leu Gln Asn Ser Ser Gly Ile Glu
            425                 430                 435

AAA TAC AAT T                                                       1361
Lys Tyr Asn
440
```

(2) INFORMATION FOR SEQ ID NO: 10:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 10:

```
Gln Tyr Ile Asn Pro Val Ala
1               5
```

-continued (2) INFORMATION FOR SEQ ID NO: 11:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 11:

```
Met Ile Thr Ile Arg Gly Ser Val His Gln Asn Phe Ala Asp Phe Th
1               5                   10                  15

Phe Ala Thr Gly
            20
```

LIPOPROTEIN ASSOCIATED PHOSPHOLIPASE A2, INHIBITORS THEREOF AND USE OF THE SAME IN DIAGNOSIS AND THERAPY

INTRODUCTION

This application is a continuation of U.S. patent application Ser. No. 10/173,233, filed Jun. 14, 2002, now issued as U.S. Pat. No. 7,052,862, which is a continuation of U.S. patent application Ser. No. 09/569,899 filed May 12, 2000, pending, which is a continuation of U.S. patent application Ser. No. 09/294,384 filed Apr. 20, 1999, issued as U.S. Pat. No. 6,177,257, which is a continuation of U.S. patent application Ser. No. 08/387,858 filed Feb. 24, 1995, issued as U.S. Pat. No. 5,981,252, which was the National Stage of International Application No. PCT/GB94/01374, filed Jun. 24, 1994, which claims benefit of priority to GB9400413.2, filed Jan. 11, 1994 and GB9313144.9 filed Jun. 25, 1993, each of which are herein incorporated by reference in their entirety.

The present invention relates to the use of inhibitors of an enzyme in the therapy, in particular in the treatment of atherosclerosis. The present invention also relates to the isolation and purification of the enzyme, to isolated nucleic acids encoding the enzyme, to recombinant host cells transformed with DNA encoding the enzyme, to the use of the enzyme in diagnosing a patient's susceptibility to atherosclerosis, and to the use of the enzyme in identifying compounds which are potentially useful for the treatment of atherosclerosis.

Lipoprotein Associated Phospholipase $A_2$ (Lp-PLA$_2$), also previously known in the art as Platelet Activating Factor Acetyl Hydrolase (PAF acetyl hydrolase). During the conversion of LDL to its oxidised form, Lp-PLA$_2$ is responsible for hydrolysing the sn-2 ester of oxidatively modified phosphatidylcholine to give lyso-phosphatidylcholine and an oxidatively modified fatty acid. Both of these products of Lp-PLA$_2$ action are potent chemoattractants for circulating monocytes. As such, this enzyme is thought to be responsible for the accumulation of cells loaded with cholesterol ester in the arteries, causing the characteristic 'fatty streak' associated with the early stages of atherosclerosis. Inhibition of the Lp-PLA$_2$ enzyme would therefore be expected to stop the build up of this fatty streak (by inhibition of the formation of lysophosphatidylcholine), and so be useful in the treatment of atherosclerosis. In addition, it is proposed that Lp-PLA$_2$ plays a direct role in LDL oxidation. This is due to the poly unsaturated fatty acid-derived lipid peroxide products of Lp-PLA$_2$ action contributing to and enhancing the overall oxidative process. In keeping with this idea, Lp-PLA$_2$ inhibitors inhibit LDL oxidation. Lp-PLA$_2$ inhibitors may therefore have a general application in any disorder that involves lipid peroxidation in conjunction with the enzyme activity, for example in addition to conditions such as atherosclerosis and diabetes other conditions such as rheumatoid arthritis, stroke, myocardial infarction, reperfusion injury and acute and chronic inflammation.

The present invention therefore provides in a first aspect an inhibitor of the enzyme lipoprotein associated Lp-PLA$_2$ for use in therapy, in particular in the treatment of atherosclerosis. Suitable compounds able to inhibit the Lp-PLA$_2$ enzyme are known in the art and include for example, the following compounds of structure (I):

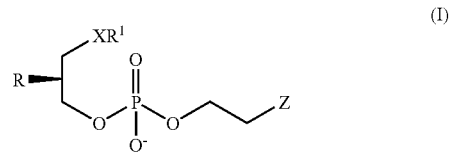

in which R is $C_{1-6}$alkylCONR$^2$;
 R$^2$ is hydrogen or $C_{1-6}$ alkyl;
 X is oxygen, sulphur or —O(CO)—;
 R$^1$ is $C_{8-20}$ alkyl;
 Z is N(R$^3$)$_2$, $^\oplus$N(R$^3$)$_3$, SR$^3$, $^\oplus$S(R$^3$)$_2$, in which each group R$^3$ is the same or different and is $C_{1-6}$ alkyl, OR$^2$, $C_{1-4}$ alkanoyl, imidazolyl or N-methylimidazolyl
 Suitably R$^2$ is hydrogen or $C_{1-6}$ alkyl; preferably R$^2$ is hydrogen.
 Suitably X is oxygen, sulphur or —(CO); preferably X is oxygen
 Suitably R$^1$ is $C_{8-20}$ alkyl; preferably R$^1$ is $C_{16-18}$ alkyl
 Suitably Z is N(R$^3$)$_2$, $^\oplus$N(R$^3$)$_3$, SR$^3$, $^\oplus$S(R$^3$)$_2$, in which each group R$^3$ is the same or different and is $C_{1-6}$ alkyl, OR$^2$, $C_{1-4}$ alkanoyl imidazolyl or N-methylimidazolyl; preferably Z is SR$^3$ in which R$^3$ is methyl or OR$^2$ in which R$^2$ is hydrogen The compounds of structure (I) can be prepared by processes known to those skilled in the art, for example as described in J Chem Soc Chem Comn., 1993, 70–72; J Org Chem, 1983, 48, 1197 and Chem Phys Lipids, 1984,35, 29–37 or procedures analogous thereto.

When used in therapy, the compounds of structure (I) are formulated in accordance with standard pharmaceutical practice.

The compounds of structure (I) and their pharmaceutically acceptable salts which are active when given orally can be formulated as liquids, for example syrups, suspensions or emulsions, tablets, capsules and, lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol oils, or water with a suspending agent, preservative, flavouring or colouring agent A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low-melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The daily dosage regimen for an adult patient may be, for example, an oral dose of between 1 mg and 500 mg, preferably-between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day. Suitably the compounds will be administered for a period of continuous therapy.

The enzyme, lipoprotein associated $Lp-PLA_2$ has not hitherto been available in isolated purified form. The present invention therefore provides in a further aspect, the enzyme lipoprotein associated $Lp-PLA_2$ in purified form. By purified form is meant at least 80%, more preferably 90%, still more preferably 95% and most preferably 99% pure with respect to other protein contaminants.

The enzyme $Lp-PLA_2$ may be characterised by one or more partial peptide sequences selected from SEQ ID NOS: 1, 2, 3, 4, 10 and 11 or by the partial peptide sequence comprising residues 271 to 441 or consisting of residues 1 to 441 of SEQ ID NO: 9. The enzyme $Lp-PLA_2$ may further or alternatively characterised by its molecular weight found to be 45 kDa, at least 45 kDa, 45–47 kDa, 46–47 kDa or 45–50 kDa The invention also provides fragments of the enzyme having $Lp-PLA_2$ activity.

The enzyme can be isolated and purified using the methods hereafter described. Once isolated, the protein sequence of the enzyme can be obtained using standard techniques. In identifying said sequence, a number of protein fragments have been identified, each of which comprises part of the whole sequence of the enzyme. These sequences are themselves novel and form a further aspect of the invention.

This invention also provides isolated nucleic acid molecules encoding the enzyme, including mRNAs, DNAs, cDNAs as well as antisense analogs thereof and biologically active and diagnostically or therapeutically useful fragments thereof.

In particular, the invention provides an isolated nucleic acid molecule consisting of bases 1 to 1361 or 38 to 1361 or comprising the sequence corresponding to bases 848 to 1361 of SEQ ID NO: 9.

This invention also provides recombinant vectors, such as cloning and expression plasmids useful as reagents in the recombinant production of the enzyme, as well as recombinant prokaryotic and/or eukaryotic host cells comprising the novel nucleic acid sequence.

This invention also provides nucleic acid probes comprising nucleic acid molecules of sufficient length to specifically hybridize to the novel nucleic acid sequences.

This invention also provides an antisense oligonucleotide having a sequence capable of binding with mRNAs encoding the enzyme so as to prevent the translation of said mRNA.

This invention also provides transgenic non-human animals comprising a nucleic acid molecule encoding the enzyme. Also provided are methods for use of said transgenic animals as models for mutation and SAR (structure/activity relationship) evaluation as well as in drug screens.

This invention further provides a method of screening compounds to identify those compounds which inhibit the enzyme comprising contacting isolated enzyme with a test compound and measuring the rate of turnover of an enzyme substrate as compared with the rate of turnover in the absence of test compound.

"Recombinant" polypeptides refer to polypeptides produced by recombinant DNA techniques, i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo: i.e, capable of replication under its own control A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e g, restriction. fragments), viruses, plasmids, and chromosomes. In discussing the structure of particular double-stranded DNA molecules, sequences may be described herein according to the normal convention of giving only the sequence in the 5' to 3' direction along the sense strand of DNA.

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" or "substantially the same" when at least about 85% (preferably at least about 90%, and most preferably at least about 95%) of the nucleotides or amino acids match over a defined length of the molecule and includes allelic variations. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See e.g., A "Current Protocols in Mol. Biol." Vol. I & II, Wiley Interscience. Ausbel et al. (ed.) (1992). Protein sequences that are substantially the same can be identified by proteolytic digestion, gel electrophoresis and microsequencing.

The term "functionally equivalent" intends that the amino acid sequence of the subject protein is one that will exhibit enzymatic activity of the same kind as that of Lp-PLA$_2$.

A "heterologous" region of a DNA construct is an identifiable segment of DNA within or attached to another DNA molecule that is not found in association with the other molecule in nature.

This invention provides an isolated nucleic acid molecule encoding the enzyme Lp-PLA$_2$. One means for isolating the coding nucleic acid is. to probe a human genomic or cDNA library with a natural or artificially designed probe using art recognized procedures (See for example: "Current Protocols in Molecular Biology", Ausubel, F. M., et al. (eds.) Greene Publishing Assoc and John Wiley Interscience, N.Y., 1989, 1992); for example using the protein fragment information disclosed herein. The enzyme of this invention may be made by recombinant genetic engineering techniques. The isolated nucleic acids particularly the DNAs can be introduced into expression vectors by operatively linking the DNA to the necessary expression control regions (e.g. regulatory regions) required for gene expression. The vectors can be introduced into the appropriate host cells such as prokaryotic (e.g., bacterial), or eukaryotic (e.g. yeast, insect or mammalian) cells by methods well known in the art (Ausubel et al., supra). The coding sequences for the desired proteins having been prepared or isolated, can be cloned into a suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), a *baculovirus* insect cell system, , YCp19 (*Saccharomyces*). See generally "DNA Cloning": Vols. I & II, Glover et al. ed IRL Press Oxford (1985) (1987) and; T. Maniatis et. al. ("Molecular Cloning" Cold Spring Harbor Laboratory (1982).

The gene can be placed under the control of a promoter, ribosome binding site (for bacterial expression) and, optionally, an operator (collectively referred to herein as "control" elements), so that the DNA sequence encoding the desire protein is transcribed into RNA in the host cell transformed by a vector containing this expression construction. The coding sequence may or may not contain a signal peptide or leader sequence. The protein sequences of the present invention can be expressed using, for example, the *E. coli* tac promoter or the protein A gene (spa) promoter and signal sequence. Leader sequences can be removed by the bacterial host in post-translational processing. See. e.g. U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the coding sequences may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site. Modification of the coding sequences may also be performed to alter codon usage to suit the chosen host cell, for enhanced expression In some cases, it may be desirable to add sequences which cause the secretion of the polypeptide from the host organism, with subsequent cleavage of the secretory signal. It may also be desirable to produce mutants or analogs of the enzyme of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See e.g., T. Maniatis et al., supra; *DNA Cloning*. Vols. I and II, supra; *Nucleic Acid Hybridization*, supra.

A number of prokaryotic expression vectors are known in the art. See. e.g., U.S. Pat. Nos. 4,578,355; 4,440,859; 4,436,815; 4,431,740; 4,431,739; 4,428,941; 4,425,437;

4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art See. e.g. U.S. Pat. Nos. 4,446,235; 4,443,539; 4,430,428; see also European Patent Applications 103,409; 100,561; 96,491. pSV2neo (as described in *J. Mol. Appl. Genet.* 1:327–341) which uses the SV40 late promoter to drive expression in mammalian cells or pCDNA1 neo, a vector derived from pCDNA1 (*Mol. Cell Biol.* 7:4125–29) which uses the CMV promoter to drive expression. Both these latter two vectors can be employed for transient or stable(using G418 resistance) expression in mammalian cells. Insect cell expression systems, e.g., *Drosophila*, are also useful, see for example, PCT applications U.S. Ser. No. 89/05155 and U.S. Ser. No. 91/06838 as well as EP application 88/3040933.

Depending on the expression system and host selected, the enzyme of the present invention may be produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates or recovered from the cell membrane fraction. Where the protein is localized to the cell surface, whole cells or isolated membranes can be used as an assayable source of the desired gene product Protein expressed bacterial hosts such as *E. coli* may require isolation from inclusion bodies and refolding. The selection of the appropriate growth conditions and recovery methods are within the skill of the art.

The identification of this novel target for the treatment of atherosclerosis, also leads to a novel diagnostic method to diagnose a patient's susceptibility to developing atherosclerotic disease.

The present invention therefore provides in a still further aspect a diagnostic method comprising isolating a sample of blood from the patient, and assaying said sample for Lp-$PLA_2$ activity. Patients that are susceptible to atherosclerotic disease are expected to have elevated levels of the Lp-$PLA_2$ enzyme, and hence the levels of Lp-$PLA_2$ provides an indication of the patients susceptibility to atherosclerotic disease. Moreover, Lp-$PLA_2$ is found located predominantly on dense subfraction(s) of LDL which are known to be very atherogenic. Plasma Lp-$PLA_2$ levels could therefore provide a ready measure of these very atherogenic small dense LDL particles.

It is expected that the presence of the enzyme in the blood sample of the patient can be assayed by analysis of enzyme activity (i.e. by an assay set up against the purified enzyme as standard); or alternatively by assaying protein content of the sample by using polyclonal or monoclonal antibodies prepared against the purified enzyme. Monoclonal (and polyclonal) antibodies raised against the purified enzyme or fragments thereof are themselves novel and form a further aspect of the invention.

DATA AND EXAMPLES

1. Screen for Lp-$PLA_2$ Inhibition.

Enzyme activity was determined by measuring the rate of turnover of the artificial substrate (A) at 37° C. in 50 mM HEPES (N-2-hydroxyethylpiperazine-N'-2-ethanesulphonic acid) buffer containing 150 mM NaCl, pH 7.4.

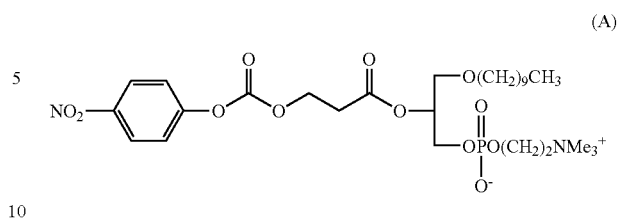

(A)

Assays were performed in 96 well titre plates.

Lp-$PLA_2$ was pre-incubated at 37° C. with vehicle or test compound for 10 min in a total volume of 180 μl. The reaction was then initiated by the addition of 20 μl 10× substrate (A) to give a final substrate concentration of 20 μM. The reaction was followed at 405 nm for 20 minutes using a plate reader with automatic mixing The rate of reaction was measured as the rate of change of absorbance.

Results:

| Compound No | $XR^1$ | R | Z | $IC_{50}(\mu M)$ |
|---|---|---|---|---|
| 1 | $O(CH_2)_{15}CH_3$ | $CH_3CONH$ | $N^+(CH_3)_3$ | 0.8 |
| 2 | $O(CH_2)_{17}CH_3$ | $CH_3CONH$ | $N^+(CH_3)_3$ | 3.5 |
| 3 | $O(CH_2)_{17}CH_3$ | $CH_3CONH$ | $S^+(CH_3)2$ | 1.0 |
| 4 | $O(CH_2)_{17}CH_3$ | $CH_3CONH$ | $SCH_3$ | 0.08 |
| 5 | $O(CH_2)_{17}CH_3$ | $CH_3CONH$ | OH | 0.45 |
| 6 | $O(CH_2)_{17}CH_3$ | $CH_3CONH$ | OAc | 0.2 |
| 7 | $O(CH_2)_{17}CH_3$ | $CH_3CONH$ | imidazole | 0.5 |
| 8 | $O(CH_2)_{17}CH_3$ | $CH_3CONH$ | N-methylimidazolium | 0.55 |
| 9 | $O(CH_2)_{17}CH_3$ | $CF_3CONH$ | $N^+(CH_3)_3$ | 2.5 |

2. Copper Stimulated LDL Oxidation:

Copper stimulated oxidation of LDL is routinely measured by following the increase in conjugated diene formation by monitoring the change in absorption at 234 nm. This assay can be used to study inhibitors of oxidative modification of LDL. FIG. 1 demonstrates that Lp-$PLA_2$ inhibitors are effective inhibitors of LDL oxidation through a prolongation of the lag phase, using compound 4 as an example.

3. Inhibition of $Cu^{2+}$ Stimulated Lyso-Phosphatidylcholine (Lyso-PtdCho) Formation.

A 1 ml aliquot of human LDL (0.25 mg protein/ml) was incubated for 15 min at 37° C. with compound or vehicle. 5 μM $Cu^{2+}$ was then added to allow oxidation/lyso-PtdCho formation to occur. The incubation was terminated by the addition of 3.75 ml chloroform/methanol/c HCl (200:400:5,v/v/v). Following the addition of 125 ml chloroform and 1.25 ml 0.1M HCl, the mixture was vortexed and centrifuged. The lower phase was carefully removed and the upper phase re-extracted with an equal volume of synthetic lower phase. The extracts were pooled and dried under nitrogen.

Phospholipids were reconstituted into 50 µl chloroform-methanol (2:1 v/v). 10 µl aliquots were spotted on to pre-run silica gel HPTLC plates and then developed in chloroform/methanol 25–30% methylamine (60:20:5 v/v/v). Plates were subsequently sprayed with the flourescent indicator, 2-p-toluidinylnaphthalene-6-sulphonic acid (1 mM in 50 mM Tris/HCl, pH 7.4) to identify phospholipid components. Fluorescence was measured at 222 nm using a CAMAG TLC scanner. Lipoprotein lyso-PtdCho content was quantified using a standard curve (0.05–0.5 µg) prepared in parallel.

Compound 4 dose dependently inhibits LDL lyso-PtdCho accumulation stimulated by copper ions with an IC$_{50}$ value of ~30 µM

4. Purification of Lipoprotein Associated Lp-PLA$_2$

Low density lipoprotein (LDL) was obtained by plasma apheresis. The LDL was dialysed against 0.5 M NaCl, 50 mM MES (4-morpholine ethane sulphonic acid), pH=6.0 overnight at 4° C. Solid CHAPS (3-[(-3-cholamidopropyl) dimethylamino]-1-propane sulphonate) was added to 10 mM and the LDL stirred for 30 minutes to effect solubilisation. The solubilised LDL was pumped onto a pre-equilibrated Blue Sepharose 6FF (Pharmacia) column (2.6×20 cm). The column was then washed with 50 mM MES, 10 mM CHAPS, 0.5 M NaCl, pH=6.0 followed by 50 mM Tris, 10 mM CHAPS, 0.5 M NaCl, pH=8.0 until the absorbance (280 nm) of the eluate reached zero. Lp-PLA$_2$ was eluted using 50 mM Tris, 10 mM CHAPS, 1.5 M NaCl, pH=8.0. The Lp-PLA$_2$ fraction was then concentrated and dialysed overnight against 50 mM Tris, 10 mM CHAPS, pH=8.0.

Figure 2:
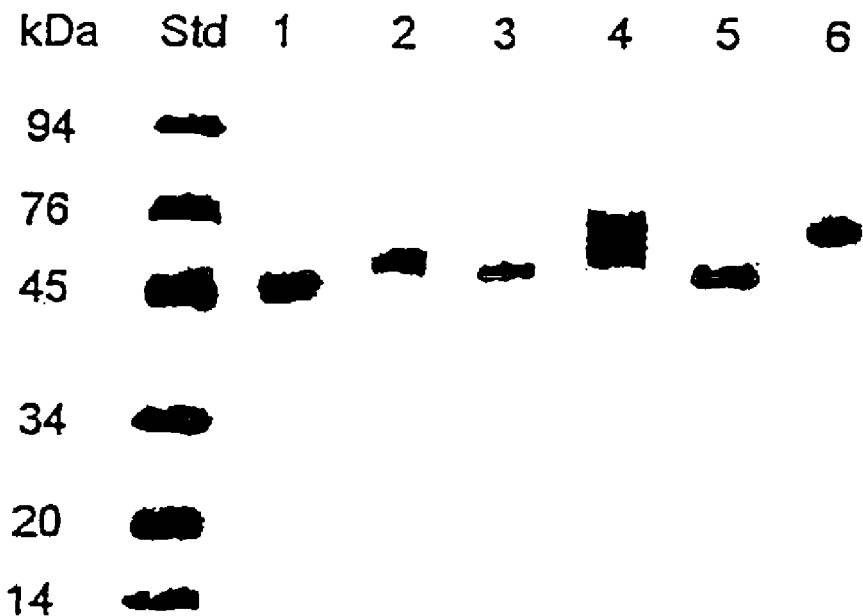

The dialysed Lp-PLA$_2$ was submitted to anion exchange chromatography on a mono Q column (Pharmacia) using 50 mM Tris, 10 mM CHAPS, pH=8.0 with a NaCl gradient from zero to 0.3 M. The Lp-PLA$_2$ fractions obtained from the mono Q column were applied directly to a Hi Trap Blue cartridge (Pharmacia). The cartridge was washed with 50 mM Tris, 10 mM CHAPS, 0.5 M NaCl, pH=8.0 until the absorbance of the eluate (280 nm) was zero. Lp-PLA$_2$ was then eluted using 50 mM Tris, 10 mM CHAPS, 1.5 M NaCl, pH=8.0. This gave Lp-PLA$_2$ which is greater than 95% pure as shown in FIG. 2. This also demonstrates that the native enzyme is extensively glycosylated.

5. Enzyme Sequence

The purity of the final enzyme preparation was verified by five criteria 1) SDS-polyacrylamide gel electrophoresis gave one band for both native and de-glycosylated forms. 2) Reverse phase high pressure liquid chromatography (RP-HPLC) gave a single peak, 3) The intact preparation gave no results by protein sequencing, implying that the protein was N-terminally blocked and free of any contaminants with open N-terminals, 4) By laser desorbtion mass spectometry only one broad peak was observed with de-glycosylated protein, and 5) none of the sections of extended peptide data from sequencing gave any database matches indicative of contaminating proteins. Three cleavage strategies were used to obtain internal sequence information; trypsin (after de-glycosylation), cyanogen bromide (methionine cleavage) and BNPS-Skatol (tryptophan cleavage). The resulting peptides were separated by RP-HPLC, collected and sequenced. The accumulated sequence data allowed several extended stretches of primary structure of the Lp-PLA2 enzyme to be verified. These are shown below as Peptides 1, 2, 3 and 4 (SEQ ID Nos 1 to 4). When searched against the National Centre for Biotechnological information (NCBI) non-redundant peptide sequence databases no high similarity matches were obtained. Estimation of the molecular weight of pure, de-glycosylated protein by laser desorption mass spectometry gives values in the region of 45–47 kDa (separately 45 kDa and 46–47 kDa), indicating that the sequences constitute approximately 15 to 20% of the protein.

6. Gene Sequence

Three expressed sequence tags (ESTs) from human cDNA libraries have been found to have extensive alignments with the Peptide Sequences 1 to 3. These EST's are shown below as Nucleotide Sequences 1 to 3 (SEQ ID NOS: 5 to 7) Nucleotide Sequence 1 is a 420 base sequence derived from a human foetal spleen library. Nucleotide Sequence 2 is a 379 base sequence derived from a 12-week human embryo library. Nucleotide Sequence 3 is a 279 base sequence derived from a T-cell lymphoma library. The identities at both the nucleic acid and amino acid level justified an overlapping alignment of the cDNA of all three ESTs, Nucleotide Sequences 3 (bases 1–278), I (bases 1–389) (in reverse orientation) and 2 (bases 1–304) with the Peptide Sequences 1, 2 and 3 (partially). Beyond these limits, the poor resolution of the raw sequence data precludes accurate base calling.

There are two remaining unassigned peptide sections from Peptides 3 and 4, both of which are expected to be present in the complete protein, -Q-Y-I-N-P-A-V-, and W-L-M-G-N-I-L-R-L-L-F-G-S-M-T-T-P-A-N-.

7. Isolation of Full-Length Lp-PLA$_2$ cDNA

The full DNA sequence was determined for the clone (HLTA145) from which the Lymphoma EST (SEQ ID NO: 7) was derived, giving a total of 572 bases; SEQ ID NO: 8. There is one base difference between this sequence and the EST (between bases 1 to 256 of the EST); at position 27 of HLTA145 there is an A compared with a T in the EST. This would cause a coding change; L in HLTA145 compared with F in the EST. Clone HLTA145 was used as a radiolabelled probe to screen the Lymphoma cDNA library in order to isolate the full-length Lp-PLA$_2$ clone. The library was prepared in the bacteriophage λ vector, Unizap XR (Stratagene).

Preparation of the Filters for Screening

The library was plated out at a density of 20,000 plaques per 150 mm petri dish onto E.coli XL-1 Blue host cells (ie. 200,000 plaques on 10 dishes). An overnight of XL-1 Blue was prepared in 100 mls LB/0.2% w/v Maltose/10 mM MgSO$_4$. The cells were pelleted, resuspended in 50 mls 10 m mM MgSO$_4$ and stored on ice. 180 µl of the library bacteriophage stock (23,400 pfu's) were added to 7 mls XL-1 Blue cells, mixed and divided into 10 aliqouts of 615 µl. The 10 tubes were incubated at 37° C. for 30 minutes. 7 mls of molten (@45° C.) top agarose (0.7% wv agarose in LB) were added, mixed well and poured onto 150 mm LB agar plates (1.5% w/v agar in LB). The plates were inverted and incubated at 37° C. for approximately 7.5 hour. The plates were held at 4° C. until needed.

The plaques were transfered to 132 mm Hybond-N nylon filters (Amersham International) by laying the filters on the plates for 2 minutes (4 minutes for the duplicate). The DNA's on the filters were denatured for 2 minutes (0.5M NaCl, 1.5M NaOH), neutralised for 4 minutes (15M NaCl, 1.0M Tris pH7.4) and the filters placed on 2×SSC for 1 minute. The filters were then dried and the DNA cross-linked to the filter using a Stratalinker UV 2400 (Stratagene) at 120,000 µJoules/cm$^2$.

The filters were pre-hybridised in 1 mM EDTA, 0.5M NaHPO$_4$, 7% SDS (Church, G M. and Gilbert, W. (1984) PNAS USA 81 p1991–1995) in a Techne HB2 hybridisation oven at 55° C. for 3 hours. Each bottle contained 2 filters and 25 mls prehybridization solution.

Preparation of the Radiolabelled Probe

The probe cDNA (from HLTA 145) was excised from pBluescript II SK+/− as an approximately 600 bp EcoRI-XhoI fragment and approximately 100 ng of gel purified fragment were labelled using 1.2 MBq $^{32}$P dATP and 1.2 MBq $^{32}$P dCTP by PCR labelling using Taq DNA polymerase (Boehringer Mannheim) and primers designed to prime at the 5' and 3' ends of the EST sequence. The labelling reaction was carried out in a total volume of 200 µl and included unlabelled dNTP's at the following concentrations:

dATP 20 µM
dCTP 20 µM
dGTP 200 µM
dTTP 200 µM

The PCR reaction was carried out over 35 cycles of:
94° C. for 30 s
60° C. for 30 s
72° C. for 30 s Screening The radiolabelled probe was denatured at 98° C. for 5 minutes and divided into 10 aliquots of 20 µl. One aliquot was added per hybridisation bottle. Hybridisation was carried out over 16 hours at 55° C. The filters were washed at 60° C. (2×10 minutes) with 0.1% w/y SDS, 0.1×SSC (50 mls per wash per bottle). The filters were autoradiographed and the films (Fuji Medical X-Ray Film) developed after 5 days exposure.

Duplicate positives were progressed to a secondary screen. The plaques were cored out into 1 ml SM (100 mM NaCl, 10 mM MgSO$_4$, 1M Tris, pH7.4), titrated and plated onto 90 mm petri dishes at between 20 and 200 pfu's per dish. The secondary screen was carried out as described for the primary screen except the filters were washed at 65° C. The autoradiographs were developed after 16 hours exposure.

DNA Sequencing

The duplicated positive clones from the secondary screen were excised from the λ Unizap XR bacteriophage vector into the Bluescript phagemid (according to the Stratagene manual) for characterisation. One of the clones, carrying an insert of approximately 1.5 kb, was sequenced on both strands (using the USB Sequenase 2.0 DNA sequencing kit) by primer walking (SEQ ID NO: 9). The cDNA has an open reading frame with the potential to code for a polypeptide of 441 amino acids.

The 3' region of the full-length cDNA aligns with the HLTA145 sequence with the exception of 3 mismatches (see below). The predicted polypeptide sequence of the lymphoma Lp-PLA$_2$ is shown as SEQ ID NO: 9.

Inspection of the full length cDNA (SEQ ID NO: 9) reveals probable errors in Peptide 3. One of these errors is in the assignment of continuity between V-M which is incompatible with the perfect sequence match with the cDNA after this position. It seems likely that a short peptide, containing the sequence -Q-Y-I-N-P-, co-purified with the longer cyanogen bromide partial cleavage peptide and, by being present in greater quantity, was assigned as the major sequence and contiguous with the subsequent amino acids. The remaining section of Peptide 3 and the whole of Peptide 4 can be identified in the predicted full length enzyme sequence (SEQ ID No: 9). It thus seems likely that Peptide 3 is in fact two separate Peptides 5 (SEQ ID No:10) and 6 (SEQ ID NO: 11). The second probable error has occurred in the transcription from the raw data for Peptide 3 which on checking was consistent with Peptide 5 having the sequence -Q-Y-I-N-P-V-A, rather than Q-Y-I-N-P-A-V-.

The 3 base differences are as follows:
1) T at 859 is A in HLTA145; aminoacid change F in full-length, L in HLTA145. (Note that the original EST is identical with the full-length cDNA at position 859).
2) C at 1173 is T in HLTA145; aminoacid change A in full-length, V in HLTA145.
3) T at 1203 is C in HLTA145; aminoacid change L in full-length, S in HLTA145.

The peptide data and the Foetal Spleen EST sequence (SEQ ID NO: 5) support the full-length cDNA sequence for differences (2) and (3) although the Human Embryo EST (SEQ ID NO: 6) is identical to the Lymphoma EST (SEQ ID No: 7) at position 1173. The Human Embryo EST (SEQ ID NO: 6) has a further difference (4) corresponding to position 1245 in the full-length Lymphoma sequence (SEQ ID NO: 9)(comparison between bases 2 to 304 of the Human Embryo EST and the full-length Lymphoma cDNA).
4) A at 1245 is T in the Embryo EST (SEQ ID NO: 6)(amino acid change D to V in the Embryo EST). Peptide data covering this region supports the Lymphoma DNA sequence (SEQ ID NO: 9).

The Lp-PLA$_2$ DNA sequence from 848 to 1361 of SEQ ID NO: 9 (amino acid residues 271 to 441 of SEQ ID NO: 9) is the region for which all major data sets agree substantially, ie. the peptide data, the Foetal spleen, full-length Lymphoma and it includes the known active site and is therefore believed to be a significant characterising region for the Lp-PLA$_2$ enzyme.

The predicted MW for the fill reading frame is 50090. This in in exess of that determined for the de-glycosylated, purified protein but post-translational events could account for this discrepancy. The most likely of these are the removal of an N-terminal signal peptide and/or limited proteolytic degradation of the protein C-terminal. The latter could occur in-vivo, during purification, or under the conditions of de-glycosylation.

Diagnostic Method

A sample of blood is taken from a patient, the plasma/serum sample prepared and passed through a dextran sulphate column pre-equilibrated with 0.9% (w\v) NaCl solution. Following washes with the same salt solution Lp-PLA$_2$ is eluted with a 4.1% (w\v) NaCl solution. Heparin agarose columns can also be used with the wash and elution solutions containing 0.7% and 2.9% NaCl, respectively. Enzyme present in the sample is determined by assaying for either
(a) enzyme activity:

The substrate (A) (see structure in 1) is used to assay Lp-PLA$_2$ activity by monitoring the absorbance change at 400 nm. Purified enzyme is pre-incubated at 37° C. and substrate (50 µM) is added after 5 minutes. The absorbance change at 400 nm is monitored for 20-minutes. This substrate has previously been reported as a substrate for classical calcium-dependent PLA$_2$s. (Washburn, W. N. and Dennis, E. A., J. Amer Chem. Soc., 1990, 112, 2040–2041); or (b) protein content Total protein content (i.e. enzyme content) can be determined using polyclonal antiserum raised against purified human Lp-PLA$_2$. The antisera recognises both native and glycosylated enzyme as measured by immunoprecipitation of activity and Western Blot analysis.

Polyclonal antiserum was prepared as follows. Immunisation of rabbits involved mixing 0.5 ml of purified human Lp-PLA$_2$ (=100 μg) with an equal volume of Freund's complete adjuvant. The final emulsion was given subcutaneously in 4×0.25 ml injections. Boosting using a Freund's incomplete adjuvant antigen mixture (4×0.25 ml subcut; dosage=50 μg) took place 4 weeks later. Adequate titre was evident at between 6–8 weeks from initial injection.

IN THE FIGURES

FIG. 1 is a graph of absorbance at 234 nm against time (min) in a study of inhibition of copper (5 μM)- stimulated LDL (150 μg/ml) oxidation by compound 4 vs control vehicle.

FIG. 2 is an analysis the purified Lp-PLA$_2$ material of Example 4 following separation by polyacrylamide gel electrophoresis. Lanes 2, 4 and 6 contain adjacent fractions of purified native Lp-PLA$_2$. Lanes 1, 3 and 5 are fractions 2, 4 and 6 respectively after N-deglycosylation.

SEQUENCE DATA

```
SEQ. ID. No: 1 - Peptide 1
-M-L-K-L-K-G-D-I-D-S-N-A-A-I-D-L-S-N-K-A-S-L-A-F-L-Q-K-H-L-
G-L-H-K-D-F-D-Q-

SEQ. ID. No: 2 - Peptide 2
-W-M-F-P-L-G-D-E-V-Y-S-R-I-P-Q-P-L-F-F-I-N-S-E-Y-F-Q-Y-
P-A-N-

SEQ. ID. No: 3 - Peptide 3
-Q-Y-I-N-P-A-V-M-I-T-I-R-G-S-V-H-Q-N-F-A-D-F-T-F-A-T-G-

SEQ. ID. No: 4 - Peptide 4
-W-L-M-G-N-I-L-R-L-L-F-G-S-M-T-T-P-A-N

SEQ. ID. No: 5 - Nucleotide Sequence 1
   1 AAAAAACCTA TTTTAATCCT AATTGTATTT CTCTATTCCT GAAGAGTTCT
  51 GTAACATGAT GTGTTGATTG GTTGTGTTAA TGTTGGTCCC TGGAATAAGA
 101 TTCTCATCAT CTCCTTCAAT CAAGCAGTCC CACTGATCAA AATCTTTATG
 151 AAGTCCTAAA TGCTTTTGTA AGAATGCTAA TGAAGCTTTG TTGCTAAGAT
 201 CAATAGCTGC ATTTGAATCT ATGTCTCCCT TTAATTTGAG CATGTGTCCA
 251 ATTATTTTGC CAGTNGCAAA AGTGAAGTCA GCAAAATTCT GGTGGACTGA
 301 ACCCCTGATT GTAATCATCT TTCTTTCTTT ATCAGGTGAG TAGCATTTTT
 351 TCATTTTTAT GATATTAGCA GGATATTGGA AATATTCAGN GTTGNTAAAA
 401 AGNGGNGGCT GAGGGATTCT SEQ. ID. No: 6 - Nucleotide Sequence 2
   1 TGCTAATATC ATAAAAATGA AAAAATGCTA CTCACCTGAT AAAGAAAGAA
  51 AGATGATTAC AATCAGGGGT TCAGTCCACC AGANTTTTGC TGACTTCACT
 101 TTTGCAACTG GCAAAATAAT TGGACACATG CTCAAATTAA AGGGAGACAT
 151 AGATTCAAAT GTAGCTATTG ATCTTAGCAA CAAAGCTTCA TTAGCATTCT
 201 TACAAAAGCA TTTAGGACTT CATAAAGATT TTGTTCAGTG GGACTGCTTG
 251 ATTGAAGGAG ATGATGAGAA TCTTATTCCA GGGACCAACA TTAACACAAC
 301 CAATTCAACA CATCATGTTT ACAGAACTTC TTCCAGGGAA TAGGAGGAAA
 351 TACAATTGGG GTTTAAAATA GGTTTTTTT SEQ. ID. No: 7 - Nucleotide Sequence 3
   1 GAAGAATGCA TTAGATTTAA AGTTTGATAT GGAACAACTG AAGGACTCTA
  51 TTGATAGGGA AAAAATAGCA GTAATTGGAC ATTCTTTTGG TGGAGCAACG
 101 GTTATTCAGA CTCTTAGTGA AGATCAGAGA TTCAGATGTG GTATTGCCCT
 151 GGATGCATGG ATGTTTCCAC TGGGTGATGA AGTATATTCC AGAATTCCTC
```

-continued

```
201 AGCCCCTCTT TTTTATCAAC TCTGAATATT TCCAATATCC TGCTAATATC

251 ATAAAANTGG AAAAATGCTA CTCACCTGG
```

Seq. ID. No:8 - DNA sequence of HLTA145
```
             10         20         30         40         50
     AAAATAGCAG TAATTGGACA TTCTTTAGGT GGAGCAACGG TTATTCAGAC 60         70         80         90        100
     TCTTAGTGAA GATCAGAGAT TCAGATGTGG TATTGCCCTG GATGCATGGA 110        120        130        140        150
     TGTTTCCACT GGGTGATGAA GTATATTCCA GAATTCCTCA GCCCCTCTTT 160        170        180        190        200
     TTTATCAACT CTGAATATTT CCAATATCCT GCTAATATCA TAAAAATGAA 210        220        230        240        250
     AAAATGCTAC TCACCTGATA AAGAAAGAAA GATGATTACA ATCAGGGGTT 260        270        280        290        300
     CAGTCCACCA GAATTTTGCT GACTTCACTT TTGCAACTGG CAAAATAATT 310        320        330        340        350
     GGACACATGC TCAAATTAAA GGGAGACATA GATTCAAATG TAGCTATTGA 360        370        380        390        400
     TCTTAGCAAC AAAGCTTCAT CAGCATTCTT ACAAAAGCAT TTAGGACTTC 410        420        430        440        450
     ATAAAGATTT TGATCAGTGG GACTGCTTGA TTGAAGGAGA TGATGAGAAT 460        470        480        490        500
     CTTATTCCAG GGACCAACAT TAACACAACC AATCAACACA TCATGTTACA 510        520        530        540        550
     GAACTCTTCA GGAATAGAGA AATACAATTA GGATTAAAAT AGGTTTTTTA 560        570
     AAAAAAAAAA AAAAAAACT CG
```

SEQ. ID. No:9 - cDNA Sequence of Lymphoma Lp-PLA$_2$
```
             10         20         30         40         50
     TGAGAGACTAAGCTGAAACTGCTGCTCAGCTCCCAAGATGGTGCCACCCA
                                          M  V  P  P  K 60         70         80         90        100
     AATTGCATGTGCTTTTCTGCCTCTGCGGCTGCCTGGCTGTGGTTTATCCT
      L  H  V  L  F  C  L  C  G  C  L  A  V  V  Y  P 110        120        130        140        150
     TTTGACTGGCAATACATAAATCCTGTTGCCCATATGAAATCATCAGCATG
      F  D  W  Q  Y  I  N  P  V  A  H  M  K  S  S  A  W 160        170        180        190        200
     GGTCAACAAAATACAAGTACTGATGGCTGCTGCAAGCTTTGGCCAAACTA
      V  N  K  I  Q  V  L  M  A  A  A  S  F  G  Q  T  K 210        220        230        240        250
     AAATCCCCCGGGGAAATGGGCCTTATTCCGTTGGTTGTACAGACTTAATG
      I  P  R  G  N  G  P  Y  S  V  G  C  T  D  L  M 260        270        280        290        300
     TTTGATCACACTAATAAGGGCACCTTCTTGCGTTTATATTATCCATCCCA
      F  D  H  T  N  K  G  T  F  L  R  L  Y  Y  P  S  Q 310        320        330        340        350
     AGATAATGATCGCCTTGACACCCTTTGGATCCCAAATAAAGAATATTTTT
      D  N  D  R  L  D  T  L  W  I  P  N  K  E  Y  F  W 360        370        380        390        400
     GGGGTCTTAGCAAATTTCTTGGAACACACTGGCTTATGGGCAACATTTTG
         G  L  S  K  F  L  G  T  H  W  L  M  G  N  I  L 410        420        430        440        450
     AGGTTACTCTTTGGTTCAATGACAACTCCTGCAAACTGGAATTCCCCTCT
      R  L  L  F  G  S  M  T  T  P  A  N  W  N  S  P  L
```

```
            460         470         480         490         500
GAGGCCTGGTGAAAAATATCCACTTGTTGTTTTTCTCATGGTCTTGGGG
  R   P   G   E   K   Y   P   L   V   V   F   S   H   G   L   G   A 510         520         530         540         550
CATTCAGGACACTTTATTCTGCTATTGGCATTGACCTGGCATCTCATGGG
  F   R   T   L   Y   S   A   I   G   I   D   L   A   S   H   G 560         570         580         590         600
TTTATAGTTGCTGCTGTAGAACACAGAGATAGATCTGCATCTGCAACTTA
  F   I   V   A   A   V   E   H   R   D   R   S   A   S   A   T   Y 610         620         630         640         650
CTATTTCAAGGACCAATCTGCTGCAGAAATAGGGGACAAGTCTTGGCTCT
  Y   F   K   D   Q   S   A   A   E   I   G   D   K   S   W   L   Y 660         670         680         690         700
ACCTTAGAACCCTGAAACAAGAGGAGGAGACACATATACGAAATGAGCAG
  L   R   T   L   K   Q   E   E   E   T   H   I   R   N   E   Q 710         720         730         740         750
GTACGGCAAAGAGCAAAAGAATGTTCCCAAGCTCTCAGTCTGATTCTTGA
  V   R   Q   R   A   K   E   C   S   Q   A   L   S   L   I   L   D 760         770         780         790         800
CATTGATCATGGAAAGCCAGTGAAGAATGCATTAGATTTAAAGTTTGATA
  I   D   H   G   K   P   V   K   N   A   L   D   L   K   F   D   M 810         820         830         840         850
TGGAACAACTGAAGGACTCTATTGATAGGGAAAAAATAGCAGTAATTGGA
  E   Q   L   K   D   S   I   D   R   E   K   I   A   V   I   G 860         870         880         890         900
CATTCTTTTGGTGGAGCAACGGTTATTCAGACTCTTAGTGAAGATCAGAG
  H   S   F   G   G   A   T   V   I   Q   T   L   S   E   D   Q   R 910         920         930         940         950
ATTCAGATGTGGTATTGCCCTGGATGCATGGATGTTTCCACTGGGTGATG
  F   R   C   G   I   A   L   D   A   W   M   F   P   L   G   D   E 960         970         980         990         1000
AAGTATATTCCAGAATTCCTCAGCCCCTCTTTTTTATCAACTCTGAATAT
  V   Y   S   R   I   P   Q   P   L   F   F   I   N   S   E   Y 1010        1020        1030        1040        1050
TTCCAATATCCTGCTAATATCATAAAAATGAAAAAATGCTACTCACCTGA
  F   Q   Y   P   A   N   I   I   K   M   K   K   C   Y   S   P   D 1060        1070        1080        1090        1100
TAAAGAAAGAAAGATGATTACAATCAGGGGTTCAGTCCACCAGAATTTTG
  K   E   R   K   M   I   T   I   R   G   S   V   H   Q   N   F   A 1110        1120        1130        1140        1150
CTGACTTCACTTTTGCAACTGGCAAAATAATTGGACACATGCTCAAATTA
  D   F   T   F   A   T   G   K   I   I   G   H   M   L   K   L 1160        1170        1180        1190        1200
AAGGGAGACATAGATTCAAATGCAGCTATTGATCTTAGCAACAAAGCTTC
  K   G   D   I   D   S   N   A   A   I   D   L   S   N   K   A   S 1210        1220        1230        1240        1250
ATTAGCATTCTTACAAAAGCATTTAGGACTTCATAAAGATTTTGATCAGT
  L   A   F   L   Q   K   H   L   G   L   H   K   D   F   D   Q   W 1260        1270        1280        1290        1300
GGGACTGCTTGATTGAAGGAGATGATGAGAATCTTATTCCAGGGACCAAC
  D   C   L   I   E   G   D   D   E   N   L   I   P   G   T   N 1310        1320        1330        1340        1350
ATTAACACAACCAATCAACACATCATGTTACAGAACTCTTCAGGAATAGA
  I   N   T   T   N   Q   H   I   M   L   Q   N   S   S   G   I   E

1360
GAAATACAATT
  K   Y   N
```

-continued

SEQ. ID. No: 10 - Peptide 5
-Q-Y-I-N-P-V-A-

SEQ. ID. No: 11 - Peptide 6
-M-I-T-I-R-G-S-V-H-Q-N-F-A-D-F-T-F-A-T-G-

The invention claimed is:

1. A method of diagnosing a patients susceptibility to atherosclerotic disease which comprises assaying a sample from a patient for Lp-PLA$_2$ enzyme activity wherein elevated Lp-PLA$_2$ enzyme activity in the sample of the patient as compared to a standard is indicative of the patient's susceptibility to atherosclerotic disease.

2. The method according to claim 1 wherein the atherosclerotic disease is selected from the group comprising atherosclerosis, stroke and myocardial infarction.

3. The method according to claim 1 wherein the atherosclerotic disease is atherosclerosis.

4. The method according to claim 1 wherein the atherosclerotic disease is stroke.

5. The method according to claim 1 wherein the atherosclerotic disease is myocardial infarction.

6. The method according to claim 1 wherein the sample is selected from the group comprising blood, serum and plasma.

7. The method according to claim 1 wherein the sample is blood.

8. The method according to claim 1 wherein the sample is serum.

9. The method according to claim 1 wherein the sample is plasma.

10. The method according to claim 1 wherein the sample is assayed in a 96 well titre plate.

11. The method of according to claim 1 wherein the sample is assayed for enzymatic activity via an absorbance assay.

12. The method according to claim 11 wherein absorbance at 400 nm or 405 nm is monitored.

13. The method of according to claim 1 wherein the sample is assayed for enzymatic activity via an absorbance assay measuring rate of turnover of an artificial substrate.

14. The method according to claim 13 wherein absorbance at 400 nm or 405 nm is monitored.

15. The method according to claim 13 wherein the artificial substrate comprises a nitrophenyl group.

16. A method of diagnosis of a patient's susceptibility to atherosclerotic disease which comprises analyzing a sample from a patient for the presence of the enzyme Lp-PLA$_2$ by assaying the sample for enzyme activity via an absorbance assay measuring rate of turnover of an artificial substrate wherein elevated Lp-PLA$_2$ enzyme activity in the sample of the patient as compared to a standard are indicative of the patient's susceptibility to atherosclerotic disease.

17. The method of claim 16 wherein the artificial substrate comprises a nitrophenyl group.

18. A method according to claim 16 wherein the disease is atherosclerosis, stroke or myocardial infarction.

19. The method according to claim 16 wherein the sample is selected from the group consisting of blood, serum, and plasma.

20. The method according to claim 16 wherein the sample is blood.

21. The method according to claim 16 wherein the sample is plasma.

22. The method according to claim 16 wherein the sample is serum.

23. The method according to claim 16 wherein the disease is atherosclerosis.

24. The method according to claim 16 wherein the disease is stroke.

25. The method according to claim 16 wherein the disease is myocardial infarction.

26. The method according to claim 16 wherein the absorbance assay is performed in a 96 well titre plate.

27. The method according to claim 16 wherein absorbance at 400 nm or 405 nm is monitored.

* * * * *